United States Patent
Riedel et al.

(10) Patent No.: US 8,821,481 B2
(45) Date of Patent: Sep. 2, 2014

(54) APPARATUS FOR OPHTHALMIC LASER SURGERY

(75) Inventors: Peter Riedel, Nürnberg (DE); Christof Donitzky, Eckental (DE)

(73) Assignee: Wavelight GmbH (DE)

( * ) Notice: Subject to any disclaimer, the term of this patent is extended or adjusted under 35 U.S.C. 154(b) by 0 days.

(21) Appl. No.: 13/394,841

(22) PCT Filed: Sep. 30, 2009

(86) PCT No.: PCT/EP2009/007030
§ 371 (c)(1),
(2), (4) Date: Mar. 8, 2012

(87) PCT Pub. No.: WO2011/038748
PCT Pub. Date: Apr. 7, 2011

(65) Prior Publication Data
US 2012/0172855 A1   Jul. 5, 2012

(51) Int. Cl.
| A61F 9/01 | (2006.01) |
| A61B 18/20 | (2006.01) |
| A61F 9/008 | (2006.01) |
| A61F 9/009 | (2006.01) |

(52) U.S. Cl.
CPC ............ *A61F 9/008* (2013.01); *A61F 9/00825* (2013.01); *A61F 2009/00872* (2013.01); *A61F 9/009* (2013.01)
USPC .......................................................... 606/5

(58) Field of Classification Search
USPC ...................................................... 606/4, 5
See application file for complete search history.

(56) References Cited

U.S. PATENT DOCUMENTS

| 5,549,632 | A  | * | 8/1996 | Lai .................................... 606/5 |
| 6,099,522 | A  | * | 8/2000 | Knopp et al. .................... 606/10 |
| 6,592,601 | B1 | * | 7/2003 | Toh et al. ....................... 606/166 |
| 2005/0192562 | A1 | * | 9/2005 | Loesel et al. ..................... 606/5 |
| 2006/0195076 | A1 | * | 8/2006 | Blumenkranz et al. .......... 606/4 |
| 2007/0078308 | A1 | * | 4/2007 | Daly ............................. 600/310 |
| 2008/0086048 | A1 | * | 4/2008 | Dupps et al. .................. 600/405 |

FOREIGN PATENT DOCUMENTS

| EP | 0697611 B1 | 9/2002 |
| WO | 2006050424 A2 | 11/2005 |
| WO | 2006074469 A2 | 7/2006 |

OTHER PUBLICATIONS

Izatt, J.A. et al, "Micrometer-Scale Resolution Imaging of the Anterior Eye in Vivo With Optical Coherence Tomography", ARCH Ophthalmol., Dec. 1994, 1584-89, vol. 112.

* cited by examiner

*Primary Examiner* — Gary Jackson
*Assistant Examiner* — Boniface N Nganga

(57) ABSTRACT

An apparatus for ophthalmic laser surgery includes a contact surface for shaping abutment of an eye to be treated, a first radiation-source for making a treatment laser beam available, optical components for directing the treatment laser beam through the contact surface onto the eye, and also a measuring instrument for measuring the depth of the anterior chamber of the eye bearing against the contact surface, whereby the measuring instrument makes measured data available that are representative of the depth of the anterior chamber of the eye at least one point of the same. The apparatus enables a monitoring of the depth of the anterior chamber for a predetermined limiting value being fallen short of and in this way can prevent a dangerous close approach of the posterior surface of the cornea to the anterior surface of the lens when the eye is pressed against the contact surface.

11 Claims, 1 Drawing Sheet

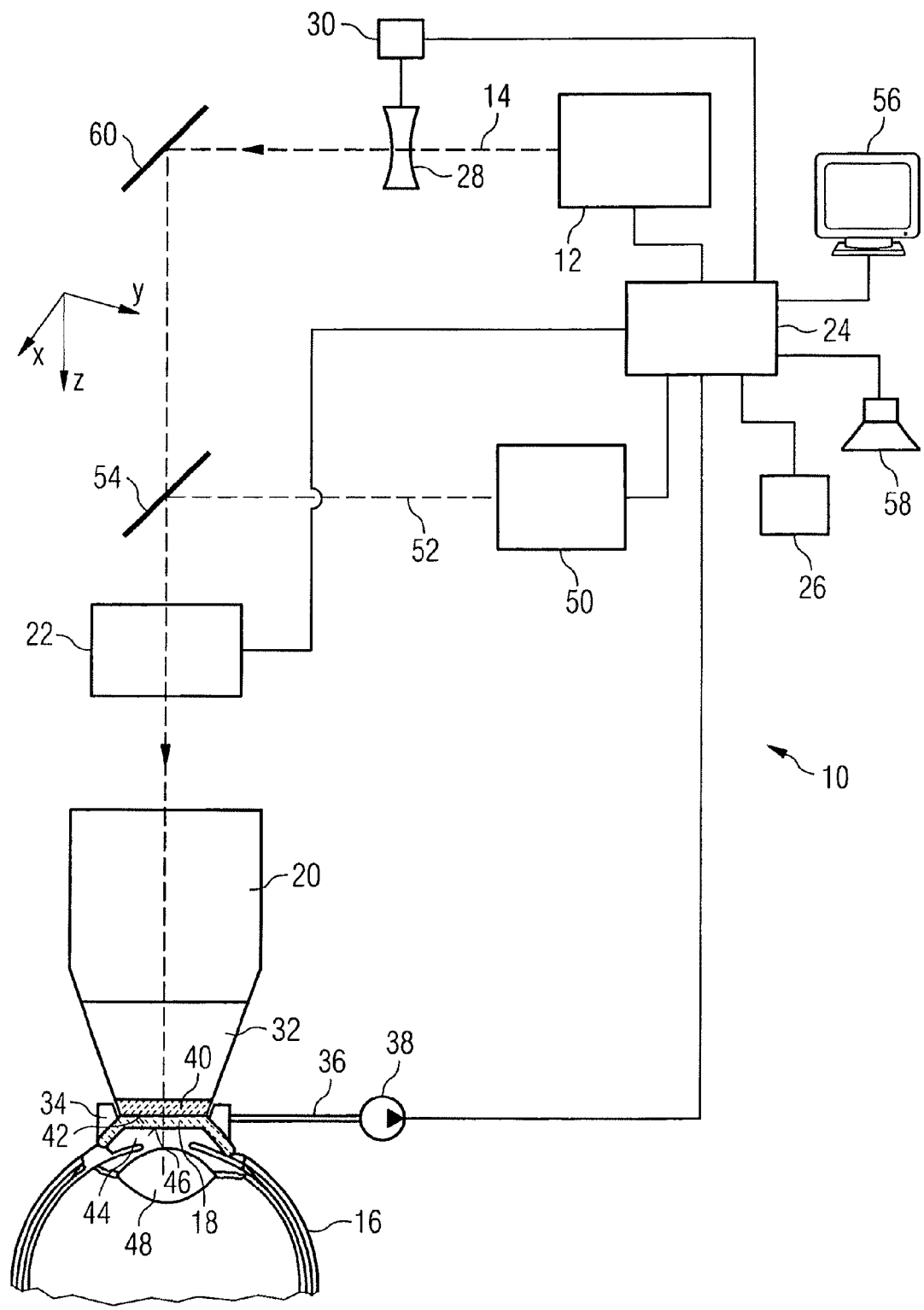

APPARATUS FOR OPHTHALMIC LASER SURGERY

This is a United States national phase application of co-pending international application number PCT/EP2009/007030 filed on Sep. 30, 2009, the disclosure of which is incorporated herein by reference.

The invention relates to an apparatus for ophthalmic laser surgery.

SUMMARY

Pulsed laser radiation finds application in numerous techniques for treatment of the human eye. In some of these techniques the eye to be treated is pressed against a transparent contact element which, with its contact surface facing towards the eye, constitutes a reference surface which is to enable a precise positioning of the beam focus in the eye in the z-direction. In this connection The 'z-direction' means, in conformity with the notation that is customary in the specialist field, the direction of propagation of the laser beam. The plane orthogonal to this direction, on the other hand, is customarily designated as the x-y plane. In particular, treatment techniques that serve for generating incisions in the ocular tissue by means of focused femtosecond laser radiation (the generation of an incision in the human eye by means of pulsed femtosecond laser radiation is always based on the effect of so-called laser-induced optical breakthrough, which results in a photodisruption) frequently make use of such contact elements, in order thereby to define unambiguously the position of the anterior surface of the eye in the coordinate system of the laser apparatus. By the contact element being pressed against the eye in such a way that a closely fitting planar abutment of the eye arises on the contact surface of the contact element facing towards the eye, the contact element presets the z-position of the anterior surface of the eye.

One form of treatment in which a corneal incision is generated by laser technology is so-called fs LASIK. In this form of treatment a small anterior cover disc of the cornea, designated in the specialist field as a flap, is cut free by means of femtosecond laser radiation. Subsequently, as in the classical LASIK technique (LASIK: Laser In Situ Keratomileusis), the flap which is still attached to the remaining corneal tissue in a hinge region is folded aside, and the tissue exposed in this way is machined in ablating manner by means of UV laser radiation. Another form of treatment is so-called corneal lenticle extraction, in which a small lenticular disc is excised within the corneal tissue by means of femtosecond laser radiation. This small disc is subsequently taken away through an additional incision which is guided out to the surface of the eye; the additional incision is produced either by means of a scalpel or likewise by means of femtosecond laser radiation.

The two types of treatment elucidated (fs LASIK, corneal lenticle extraction) are to be understood as being purely exemplary. Generally, the invention is applicable in any treatment techniques in which the eye is pressed against a contact surface, in order by this means to define the position of the anterior surface of the eye within the coordinate system of the laser apparatus.

The pressing of the eye against the contact surface gives rise to a deformation of the cornea. Depending on the shape of the contact surface, this can result in an at least local shortening of the anterior chamber—that is to say, in a smaller depth of the anterior chamber. The anterior chamber is the space between the cornea and the lens of the human eye. In a normal, undeformed human eye the depth of the anterior chamber customarily amounts, on average, to approximately 2 mm to 4 mm. Particularly in the case of a levelling of the cornea by abutment against a flat contact surface (applanation surface), the deformation of the cornea may be so great that the latter comes dangerously close to the anterior surface of the human lens. A reciprocal contact between the posterior surface of the cornea (endothelium) and the anterior surface of the lens is to be avoided at all costs. It could damage the corneal endothelial layer and give rise to opacities in the cornea.

The object of the invention is to make available an apparatus for ophthalmic laser surgery that in the course of the implementation of laser treatments of the human eye in which the eye is pressed against a contact surface offers a high degree of security that no undesirable damage will occur to the corneal endothelium.

With a view to achieving this object, in accordance with the invention an apparatus for ophthalmic laser surgery is provided, including a contact surface for shaping abutment of an eye to be treated, a first radiation-source providing a treatment laser beam, optical components for directing the treatment laser beam through the contact surface onto the eye, and a measuring device for measuring the depth of the anterior chamber of the eye bearing against the contact surface, whereby the measuring instrument provides measured data available that are representative of the depth of the anterior chamber of the eye at least one point of the same.

The invention teaches to survey the depth of the anterior chamber while the eye is pressed against the contact surface and the cornea is accordingly deformed. In particular, the measurement of the depth of the anterior chamber may be undertaken repeatedly before, during or/and after a laser treatment, for example continuously or at regular temporal intervals, in order to be able to detect any changes in the depth of the anterior chamber rapidly. A measurement of the depth of the anterior chamber is advisable, in particular, in the phase in which the eye and the contact surface are brought relatively closer together in order to establish the shaping abutment of the eye on the contact surface. This relative approach may, for example, be undertaken by mechanical or manual movement of a patient adapter bearing the contact surface or/and of a couch on which the patient is lying. Expediently, in the course of the relative approach of the contact surface and the eye the depth of the anterior chamber is surveyed several times, for example until a predetermined minimum value of the depth of the anterior chamber is attained that on no account may be fallen short of. This minimum value should be chosen in such a way that there is an adequate safety distance between the posterior surface of the cornea and the anterior surface of the lens.

In a preferred embodiment the measuring device (instrument) includes a second radiation-source providing a measuring beam, the optical components being designed and arranged to direct also the measuring beam through the contact surface onto the eye. This guarantees that a survey of the depth of the anterior chamber is possible in a state in which the eye is pressed against the contact surface.

It may be sufficient to survey the depth of the anterior chamber only at a single, suitably chosen point in the x-y plane, for example at an applanation centre or at least in the vicinity of such applanation centre. For enhanced safety, however, it may be advantageous if the measuring instrument is designed to measure the depth of the anterior chamber at various points of the eye. For example, the measuring instrument can measure the depth of the anterior chamber at a plurality of predetermined measuring points. These measuring points may, for example, include a central measuring point and also a plurality of peripheral measuring points distributed in a circle or in several concentric circles around the central measuring point. Alternatively, a scanning survey of the depth of the anterior chamber is also conceivable in which the measuring instrument scans at least a predetermined measuring region of the eye with a plurality of scan points situated closely alongside one another and measures the depth of the anterior chamber at each of these scan points. Such a scanning survey of the depth of the anterior chamber permits a high resolution and, so to speak, a planar mapping of the depth of the anterior chamber.

Preferentially connected to the measuring instrument is an electronic evaluating and control arrangement which has been set up to examine the depth of the anterior chamber, represented by the measured data, for at least one predetermined value being fallen short of and, depending on the falling short of the predetermined value, to bring about a predetermined action. This enables an automatic monitoring of the depth of the anterior chamber and the automatic initiation of suitable actions, should the depth of the anterior chamber fall short of the predetermined value. It will be understood that several different predetermined limiting values may have been defined which, so to speak, represent a different degree of danger. The smaller the spacing between the posterior surface of the cornea and the anterior surface of the lens becomes, the more urgent or massive the automatic reaction brought about by the evaluating and control arrangement may be.

For example, the evaluating and control arrangement may have been set up to bring about the output of an optical or/and acoustic warning in the case where the predetermined value is fallen short of.

Alternatively or additionally, the evaluating and control arrangement may have been set up to control, in the case where the predetermined value is fallen short of, at least one controllable component in the sense of a halt of a relative approaching movement between the contact surface and the eye or in the sense of a relative movement apart of the contact surface and the eye. The controllable component may be, for example, an evacuating pump which generates an underpressure by means of which the contact surface is held on the eye or/and a patient adapter bearing the contact surface is held on a suction ring mounted onto the eye. As a result of reduction or even complete removal of the underpressure, the abutment pressure of the eye on the contact surface can be reduced. Under certain circumstances the contact surface can even be detached from the eye. In each case, in this manner the posterior surface of the cornea can be taken away out of a possibly dangerously close position to the anterior surface of the lens.

Furthermore, alternatively or additionally it is possible that the evaluating and control arrangement has been set up to permit the emission of the treatment laser beam in a manner depending on the depth of the anterior chamber, represented by the measured data, not falling short of the predetermined value. Conversely, the evaluating and control arrangement may be able to switch off the treatment laser beam as soon as the measured depth of the anterior chamber falls short of the predetermined value.

The measuring instrument may include an optical interferometer which has been set up to cause the measuring beam and a reflection coming back from the eye through the contact surface to interfere. For example, the measuring instrument may be an OLCR measuring instrument—that is to say, it may operate in accordance with the principle of optical low-coherence reflectometry.

A transparent contact element constituting the contact surface may take the form either of an applanation plate or of a contact lens with non-planar abutment surface for the eye. The term 'applanation plate' in this connection is understood to mean a contact element that on its plate side facing towards the eye exhibits a flat abutment surface for the front of the eye and therefore permits a levelling of the cornea. On its plate side facing away from the eye the applanation plate may equally be flat; but it may also be concavely or convexly curved there. The term 'contact lens', on the other hand, is understood to mean a contact element that on its side facing towards the eye exhibits a non-planar abutment surface for the front of the eye. As a rule, this abutment surface will be concavely curved.

The applanation plate or the contact lens may, for example, be held on a patient adapter which is coupled with a focusing objective of the apparatus.

The pulse duration of the treatment laser beam preferentially lies within the femtosecond range.

The invention also provides a method for application in the course of the implementation of a laser surgical treatment of the human eye, whereby with this method the eye to be treated is brought into a shaping abutment contact with a contact surface and the depth of the anterior chamber of the eye bearing against the contact surface is measured, providing measured data that are representative of the depth of the anterior chamber of the eye at least one point of the same. Depending on the measured value of the depth of the anterior chamber, one or more predetermined actions can then be brought about. For example, an electronic evaluating and control arrangement can enable a treatment laser beam so long as the measured depth of the anterior chamber is not smaller than at least one predetermined value. Upon such a predetermined value being attained, the evaluating and control arrangement can alternatively or additionally bring about the output of a warning in optical or/and acoustic form. Similarly, the evaluating and control arrangement can bring about a relative movement apart of the contact surface and of the eye or at least a halt of the approach between the contact surface and the eye.

DETAILED DESCRIPTION OF THE DRAWING

The invention will be elucidated further in the following on the basis of the appended drawing. The single FIG. 1 thereof represents, in greatly schematised form, an embodiment of an apparatus for ophthalmic laser surgery. The apparatus is denoted generally by 10. It exhibits an fs laser 12 which emits a pulsed laser beam 14 with pulse durations within the femtosecond range. The laser beam 14 serves for treating a human eye 16, and there, for example, a cornea 18. In particular, it serves for generating incisions in the cornea 18, whereby the incision arises as a result of a stringing-together of intracorneal photodisruptions which are brought about in the beam focus through the effect of the laser-induced optical breakthrough.

In the beam path of the laser beam 14 there are arranged various optical components for guiding and shaping the laser beam 14. In particular, these components include a focusing objective 20 (for example, an f-theta objective) as well as a scanner 22 placed upstream of the objective 20, by means of which the laser beam 14 emitted by the laser 12 is capable of being deflected in a plane (x-y plane) orthogonal to the beam path of the laser beam in accordance with a treatment profile ascertained for the eye 16. A coordinate system which has been drawn in illustrates this plane and also a z-axis predetermined by the direction of the laser beam 14. The scanner 22 is, for example, constructed in a manner known as such from a pair of galvanometrically controlled deflecting mirrors which are respectively responsible for the deflection of the beam in the direction of one of the axes spanning the x-y plane. An electronic evaluating and control unit 24 controls the scanner 22 in accordance with a control program stored in a memory 26, which represents an incision profile to be generated in the eye 16. The incision profile in this case is represented by the coordinates of a three-dimensional pattern of scan points at which, in each instance, a photodisruption is to be brought about.

Moreover, the aforementioned optical components include at least one controllable optical element for the z-adjustment of the beam focus of the laser beam 14. In the exemplary case that is shown, this optical element 28 is constituted by a lens (in concrete terms, a diverging lens). For the purpose of controlling the lens 28, use is made of a suitable actuator 30 which in turn is controlled by the evaluating and control unit 24. For example, the lens 28 may be capable of being mechanically displaced along the beam path of the laser beam 14. Alternatively, it is conceivable to use a controllable liquid lens of variable refractive power. With z-position unchanged and also with otherwise unchanged setting of the focusing objective 20, a z-relocation of the beam focus can be obtained by displacing a longitudinally adjustable lens or by varying the refractive power of a liquid lens. It will be understood that for the z-adjustment of the beam focus other components are also conceivable, for instance a deformable mirror. On account of its comparatively higher inertia, with the focusing objective 20 it is expedient to perform only an initial basic setting of the beam focus (i.e. focusing onto a predetermined z-reference position), and to bring about the z-relocations of the beam focus predetermined by the incision profile by means of a component with quicker speed of response which is arranged outside the focusing objective 20. Such a component with quicker speed of response is, for example, the lens 28.

On the side of emergence of the beam the focusing objective 20 is coupled with a patient adapter 32 which serves for establishing a mechanical coupling between the eye 16 and the focusing objective 20. The patient adapter 32 possesses a suitable mechanical interface for coupling to a suction ring 34 which at the start of the treatment is mounted onto the eye 16 and fixed there by suction force. Accordingly, the suction ring 34 is connected via an evacuating line 36 to an evacuating pump 38 which is capable of being controlled by the electronic evaluating and control unit 24. After mounting of the suction ring 34 onto the eye 16, a relative approach of the eye 16 and the patient adapter 32 occurs until the suction ring 34 and the patient adapter 32 have been properly coupled to one another. With respect to the reciprocal coupling of the suction ring 34 and the patient adapter 32, reference may be made, for example, to international patent application PCT/EP 2008/006962, the total content of which is hereby incorporated by reference.

The patient adapter 32 serves as carrier for a transparent contact element 40 which, in the exemplary case shown, takes the form of a plane-parallel applanation plate. The patient adapter 32 includes, for example, a taper-sleeve body, at the narrower end of which (in the drawing, the lower end) the applanation plate 34 is arranged. In the region of the wider end of the sleeve (in the drawing, the upper end), on the other hand, the patient adapter 32 is attached to the focusing objective 20 and possesses there suitable structures which permit a, where desired, releasable fixing of the patient adapter 32 to the focusing objective 20.

Because it comes into contact with the eye 16 during the treatment, the applanation plate 40 is, from the standpoint of hygiene, a critical article which is therefore expediently to be exchanged after each treatment. For this purpose, the applanation plate 40 may have been exchangeably fitted to the patient adapter 32. Alternatively, the patient adapter 32 together with the applanation plate 40 may constitute a disposable unit or at least a unit that is intended for once-only use and then to be sterilised again for further use. In this case the applanation plate 40 may have been permanently connected to the patient adapter 32.

In any case, the underside of the applanation plate 40 facing towards the eye constitutes a flat contact surface 42, against which the eye 16 has to be pressed. This brings about a levelling of the anterior surface of the eye (generally, a deformation of the cornea 18 of the eye 16). The levelling of the anterior surface of the eye has the effect that at least in the levelled region the depth of the anterior chamber of the eye denoted by 44 decreases; the posterior surface of the cornea—denoted by 46—approaches there the anterior surface of the human lens denoted by 48.

In order that the posterior surface 46 of the cornea does not come dangerously close to the anterior surface of the lens, the laser surgical apparatus 10 exhibits an optical-coherence interferometric measuring instrument 50, which is preferentially an OLCR measuring instrument. The measuring instrument 50 emits a measuring beam 52 which by means of an immovably arranged, semi-transparent deflecting mirror 54 is coupled into the beam path of the laser beam 14. The measuring beam 52 passes through the focusing objective 20, the patient adapter 32 and also the applanation plate 40 and impinges on the eye 16. The incidence of the measuring beam 52 on the eye brings about reflections. The latter find their way back to the measuring instrument 50 on the same path that the measuring beam 52 has taken. In an interferometer contained in the measuring instrument 40 and not represented in any detail, the measuring beam 52 is caused to interfere with the reflected beam coming back. From the measured interference data obtained in this regard, the z-dimension of the anterior chamber 44 can be ascertained. The evaluating and control unit 24 receives the measured interference data from the measuring instrument 50 and computes from these data the depth of the anterior chamber at that point in the x-y plane where the measuring beam 52 impinged.

In the exemplary case that is shown, the measuring beam 52 emitted by the measuring instrument 50 passes through the scanner 22. This makes it possible to utilise the x-y scan function of the scanner 22 also for the measuring beam 52. In this way a measurement of the depth of the anterior chamber at different points along the x-y plane is possible. This guarantees a high degree of security for registering metrologically that point or that region at which the depth of the anterior chamber is smallest. For example, the measurement of the depth of the anterior chamber can be carried out in accordance with a pattern that provides a central measuring point as well as further measuring points which are distributed in one or more concentric circles around the central measuring point. The control of the location of the measuring beam in the x-y plane that is necessary for this can expediently be obtained with the scanner 22.

In one configuration the scanner 22 may contain a pair of mirrors or a deflecting unit operating in accordance with a different scanning technique, which is utilised jointly for the x-y deflection of the laser beam 14 and of the measuring beam 52. In another configuration the scanner 22 may contain separate pairs of mirrors or generally separate deflecting units, one of which is used for x-y deflection of the laser beam 14 and the other for x-y deflection of the measuring beam 52. The deflecting unit for the measuring beam 52 could, for example, be equipped with smaller, more rapidly movable mirrors than the deflecting unit for the laser beam 14. In yet another configuration, a deflecting unit for the measuring beam 52 may have been arranged in that part of the beam path of the measuring beam which lies upstream of the deflecting mirror 54.

The ascertainment of the depth of the anterior chamber may, for example, be undertaken on the basis of the spacing of defined signal peaks in an interference measuring signal generated by the measuring instrument 50. Such an interference measuring signal may show clearly protruding signal peaks which arise through reflection of the measuring beam 52 on the various boundary surfaces on which the measuring beam 52 impinges. Such a boundary surface is the front of the applanation plate 40 facing away from the eye; a further boundary surface is the contact surface 42 formed on the rear of the applanation plate 40 facing towards the eye, and yet further boundary surfaces are the posterior surface 46 of the cornea and also the anterior surface of the lens 48. The reciprocal spacing of the signal peaks is a measure of the z-spacing of the boundary surfaces in question. Therefore the evaluating and control unit 24 can easily ascertain the depth of the anterior chamber at the point in question from the spacing of the signal peaks that arise through reflection of the measuring beam 52 on the posterior surface of the cornea and on the anterior surface of the lens.

The evaluating and control unit 24 monitors the depth of the anterior chamber of the eye 16 in order to bring about suitable countermeasures in good time should the posterior surface 46 of the cornea come dangerously close to the anterior surface of the lens. The evaluating and control unit 24 preferentially monitors the depth of the anterior chamber individually at each measuring point where measurements of the depth of the anterior chamber are undertaken. If at one of the measuring points the measured value of the depth of the anterior chamber should reach a predetermined minimum value (limiting value) which is not to be fallen short of, the evaluating and control unit 24 can, for example, interrupt the supply of the suction ring 24 with underpressure by means of the pump 38, so that the patient adapter 32 can be at least partly detached from the suction ring 34, and the pressure of the applanation plate 40 on the cornea 18 becomes lower. Alternatively or additionally, the evaluating and control unit 24 can output an optical warning on a display screen 56 or on another suitable optical output means or/and can output an acoustic warning via a loudspeaker 58. Expediently the monitoring of the depth of the anterior chamber is undertaken already during the procedure of coupling the patient adapter 32 to the suction ring 34, at any rate at least immediately after this coupling procedure is concluded. In this manner it can be detected at an early stage whether the posterior surface 46 of the cornea is coming dangerously close to the lens 48. The aforementioned limiting value, from which the evaluating and control unit 24 initiates countermeasures, may, for example, correspond to a residual depth of the anterior chamber of approximately 0.5 mm.

Denoted by reference symbol 60 is a further immovable deflecting mirror which serves for guiding the treatment laser beam 14.

The invention claimed is:

1. Apparatus for ophthalmic laser surgery, including a contact surface configured to shape abutment of an eye and to be placed in contact with the eye by an underpressure,
a first radiation-source configured to provide a treatment laser beam,
optical components configured to direct the treatment laser beam through the contact surface onto the eye,
a measuring device configured to:
measure the depth of the anterior chamber of the eye bearing against the contact surface at a plurality of points distributed in a plurality of concentric circles on the eye, and
provide measured data that are representative of the depth of the anterior chamber of the eye at the points of the eye, and
an evaluating and control arrangement configured to:
determine whether the measured data falls short of a predetermined value; and
interrupt the supply of the underpressure if the measured data falls short of the predetermined value.

2. Apparatus according to claim 1, wherein the measuring device includes a second radiation-source configured to provide a measuring beam, and the optical components are designed and arranged to direct also the measuring beam through the contact surface onto the eye.

3. Apparatus according to claim 1, wherein the evaluating and control arrangement is configured to bring about the output of an optical and/or acoustic warning if the measured data falls short of the predetermined value.

4. Apparatus according to claim 1, wherein the evaluating and control arrangement is configured to halt a relative approaching movement between the contact surface and the eye or a relative movement of the contact surface from the eye if the measured data falls short of the predetermined value.

5. Apparatus according to claim 1, wherein the evaluating and control arrangement is configured to permit the emission of the treatment laser beam if the measured data does not fall short of the predetermined value.

6. Apparatus according to claim 2, wherein the measuring device includes an optical interferometer adapted to cause the measuring beam and a reflection coming back from the eye through the contact surface to interfere.

7. Apparatus according to claim 6, wherein the measuring device operates in accordance with the principle of optical low-coherence reflectometry.

8. Apparatus according to claim 1, wherein the contact surface is constituted by a transparent contact element which takes the form of an applanation plate or of a contact lens with non-planar abutment surface for the eye.

9. Apparatus according to claim 8, wherein the applanation plate or the contact lens is supported on a patient adapter which is coupled with a focusing objective of the apparatus.

10. Apparatus according to claim 1, wherein the pulse duration of the treatment laser beam lies within the femtosecond range.

11. A method comprising:
placing a contact surface in contact with an eye by an underpressure;
measuring the depth of an anterior chamber of the eye bearing against the contact surface at a plurality of points;
providing measured data that are representative of the depth of the anterior chamber of the eye at the points of the eye;
determining whether the measured data falls short of a predetermined value;
interrupting the supply of the underpressure if the measured data falls short of the predetermined value; and
providing and directing a treatment laser beam through the contact surface onto the eye if the measured data does not fall short of the predetermined value.

\* \* \* \* \*